US010154830B2

(12) United States Patent
Havel et al.

(10) Patent No.: US 10,154,830 B2
(45) Date of Patent: *Dec. 18, 2018

(54) 3D CATHETER-BASED ULTRASOUND ASSEMBLY WITH GIMBAL-MOUNT TRANSDUCER AND SINGLE COIL DRIVE

(71) Applicant: Muffin Incorporated, West Lafayette, IN (US)

(72) Inventors: William J. Havel, West Lafayette, IN (US); Peter S. McKinnis, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 510 days.

This patent is subject to a terminal disclaimer.

(21) Appl. No.: 14/815,324

(22) Filed: Jul. 31, 2015

(65) Prior Publication Data

US 2015/0335311 A1 Nov. 26, 2015

Related U.S. Application Data

(63) Continuation of application No. PCT/US2014/013850, filed on Jan. 30, 2014.

(Continued)

(51) Int. Cl.
*A61B 8/00* (2006.01)
*A61B 8/12* (2006.01)
(Continued)

(52) U.S. Cl.
CPC ............ *A61B 8/445* (2013.01); *A61B 8/0891* (2013.01); *A61B 8/12* (2013.01); *A61B 8/4461* (2013.01);
(Continued)

(58) Field of Classification Search
CPC ......... A61B 8/0891; A61B 8/12; A61B 8/445; A61B 8/4461; A61B 8/483; G01S 15/894; G01S 15/8993; G01S 7/52079
See application file for complete search history.

(56) References Cited

U.S. PATENT DOCUMENTS 4,841,979 A 6/1989 Dow et al.
5,088,495 A 2/1992 Miyagawa
(Continued)

FOREIGN PATENT DOCUMENTS

JP 2007/289315 11/2007
KR 10-2012-00054474 A 5/2012
WO WO 1993/05712 4/1993

OTHER PUBLICATIONS

English Abstract of JP 2007-289315 to Matsushita Electric Ind. Co. Ltd. Nov. 8, 2007.

(Continued)

*Primary Examiner* — Michael Rozanski
(74) *Attorney, Agent, or Firm* — Woodard, Emhardt, Moriarty, McNett & Henry LLP

(57) ABSTRACT

Described are embodiments of devices and methods for imaging a body conduit, such as a blood vessel. In particular embodiments, the catheter has a chamber within which is a transducer mounted to a pivot mechanism. A coil provides a pivot force to the transducer. A magnet is attached to the transducer and is receptive of a torque applied by a magnetic field produced by energizing of the coil. A driving mechanism receives an impact from the pivot member and causes the pivot mechanism to rotate about a rotation axis.

20 Claims, 7 Drawing Sheets

Related U.S. Application Data

(60) Provisional application No. 61/758,936, filed on Jan. 31, 2013.

(51) Int. Cl.
*A61B 8/08* (2006.01)
*G01S 15/89* (2006.01)
*G01S 7/52* (2006.01)

(52) U.S. Cl.
CPC .......... *A61B 8/483* (2013.01); *G01S 7/52079* (2013.01); *G01S 15/894* (2013.01); *G01S 15/8993* (2013.01)

(56) References Cited

U.S. PATENT DOCUMENTS

| | | |
|---|---|---|
| 8,214,010 B2 | 7/2012 | Courtney et al. |
| 9,247,925 B2 * | 2/2016 | Havel .................... A61B 8/445 |
| 2002/0143252 A1 | 10/2002 | Dunne et al. |
| 2009/0149782 A1 | 6/2009 | Cohen |
| 2014/0180120 A1 * | 6/2014 | Hossack ................ A61B 8/445 600/463 |

OTHER PUBLICATIONS

International Search Report and Written Opinion issued in PCT/US2014/013850, dated May 27, 2014.

English Abstract of KR 10-2012-00054474A to Samsung Electronics Co., Ltd., May 30, 2012.

\* cited by examiner

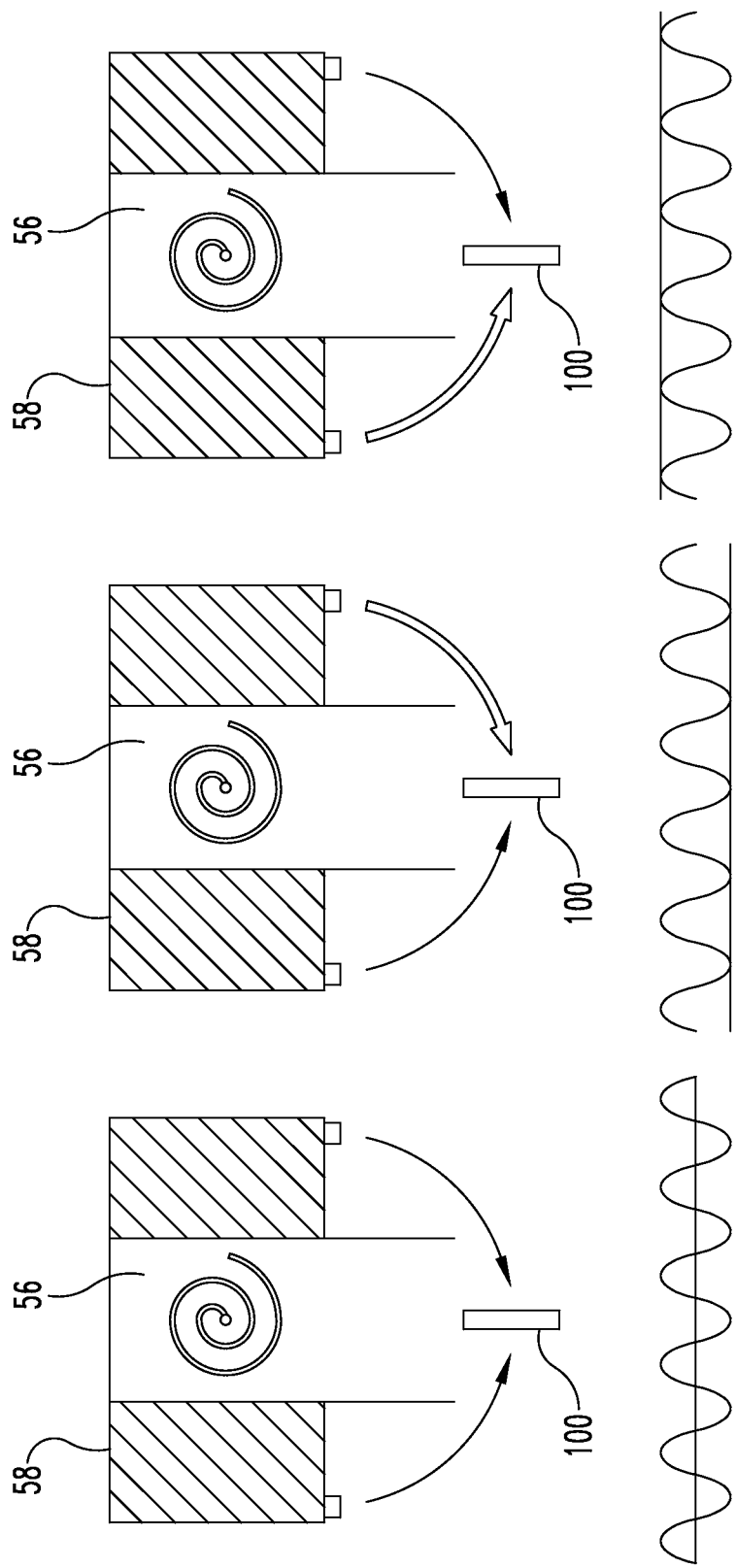

3D CATHETER-BASED ULTRASOUND ASSEMBLY WITH GIMBAL-MOUNT TRANSDUCER AND SINGLE COIL DRIVE

REFERENCE TO RELATED APPLICATION

This application is a continuation of PCT/US2014/013850, filed Jan. 30, 2014, which claims the benefit of U.S. Provisional Patent Application No. 61/758,936, filed Jan. 31, 2013, which is hereby incorporated by reference in its entirety.

FIELD OF THE DISCLOSURE

The present disclosure concerns devices and methods for ultrasound use within the human body, including devices and methods for employing ultrasound to image body areas, such as the interior of blood vessels.

BACKGROUND

Ultrasound technology has been used for therapeutic and diagnostic medical procedures, which can include providing imaging of internal portions of a body. For example, devices have been proposed for using ultrasound imaging within blood vessels to view the condition of the vessel and/or placement or condition of a device placed in the vessel. However, a number of problems with such devices remain. For example, many such devices provide at best an image of a cross section of tissue or other items of interest, i.e. a thin, disk-shaped slice of the interior of a blood vessel with a portion in the center that is not within the range of the ultrasound beam. In some other devices, the ultrasound beam is directed at a fixed angle that is not substantially perpendicular to the longitudinal axis (e.g. at 45 degrees). In this case the imaged region is static in the form of a portion of the surface of a cone, also with a center portion that is not within the range of the ultrasound beam. In either case, in order to visualize the entirety of a significant length within the body (e.g. surfaces or portions of tissue, or of devices), the device must be moved along that length, with respective images of cross sections at particular locations taken. Such movement may be inexact, and may include risks associated with blind insertion of the device through the vessel. It is also slow. Typical pull back images take on the order of 30 s to perform (at a speed of about 0.1 mm/s). Additionally, any changes in the orientation of the transducer during pullback distort the image.

Three-dimensional information provides the added value that it can be used to help in navigation of devices within the vasculature and confirmation of position of the devices. In an intravascular example, catheters can be moved up and down vessels and the image data obtained via ultrasound can be combined or otherwise processed in order to create three-dimensional information. However, the catheter tip motion and angle must be known in order to produce accurate and usable data. Three-dimensional images may be acquired by one-dimensional arrays connected to a mechanical actuator, to move the arrays within the catheter or other device. Such designs are expensive and generally require more space in a device than many vessels will permit. To achieve good image quality, such array transducers must simultaneously transmit and receive on many separate channels. That condition requires several expensive and bulky coaxial cables. Fewer coaxial cables can be used, but doing so reduces the quality of the image and image frame rate.

Ultrasound devices have been proposed which include a motion of a transducer about two axes to provide three-dimensional information. However, the mechanical mechanisms that provide such movement tend to be bulky and require dimensions which are unsuitable for applications in small body areas. Additionally, the problem of providing motion to a transducer must be solved. Designs including torque cables can be problematic. Practically, a sufficiently maneuverable torque cable creates a potential for delay in the transferring of torque from one end of the cable to the other, as the cable stores and releases elastic energy, which causes the transducer assembly to rotate at a non-uniform rate even when the rotation source rotates at a uniform rate. The non-uniform rotation rate causes the resulting data or images to be distorted. These problems are magnified if two torque cables are used for two-axis movement of the transducer. In some cases, separate motors can be used to provide movement to the transducer. However, motors require additional space and can include further disadvantages such as control wires or structural components which cross the viewing window and cause a portion of an image to be blocked. Additionally, existing feedback mechanisms for controlling complex motor motion can be costly and bulky.

There remains a need for accurate and efficient application of ultrasound in three dimensions along a substantial length of a small body area, for example to provide a physician with a real-time view along that length. There also remains a need for devices that can view a medical device and one or more tissues or tissue parts simultaneously, particularly in cases in which the device and tissue(s) could not have been imaged reliably in any two-dimensional plane.

SUMMARY

Among other things, disclosed are apparatus and methods for providing an ultrasound beam with two controllable degrees of freedom within the body of a patient. For example, such apparatuses can include a transducer for transmitting and/or receiving ultrasound signals and a pivot mechanism which is rotatable about a rotation axis. A pivot member is mounted to the pivot mechanism and pivotable about a pivot axis that is substantially perpendicular to the rotation axis. Also included is a driving mechanism positioned within the pivot path of the pivot member such that during rotation about the pivot axis a portion of the pivot member strikes the driving mechanism and causes the pivot mechanism to rotate about the rotation axis.

The medical device can include a coil positioned concentric to and along the rotation axis. The pivot member can include a magnetic layer and the transducer. The coil includes a plurality of electrically conductive windings, such that application of electric current to the coil creates a torque on the pivot member about the pivot axis. The pivot member can reciprocate alternatively between a driving pivot stroke and a non-driving pivot stroke such that driving pivot stroke causes the pivot mechanism to rotate about the rotation axis and the non-driving pivot stroke does not cause the pivot mechanism to rotate about the rotation axis. The electric current can be an alternating current. The driving pivot stroke has a torque which is larger than the torque of the non-driving pivot stroke. The electric current can include a direct current offset component to produce a difference in the torque between the driving pivot stroke and the non-driving pivot stroke.

The medical device can include an engagement surface positioned cylindrically and concentric to the rotation axis.

The driving mechanism is positioned to engage the pivot member and engagement surface. The pivot member is pivotable through a range bounded by the driving mechanism. During pivotal rotation of the pivot member, abutment of the pivot member against the driving mechanism moves the driving mechanism to engage the engagement surface. Engagement of the driving mechanism with the engagement surface causes the pivot mechanism to rotate about the rotation axis. The medical device can include a stop bar and a driving rod fixed relative to the stop bar. Stop bar has a portion position within the pivot path of the pivot member and the driving rod is positioned to engage the engagement surface when the pivot member strikes the stop bar. Alternatively, the medical device can include a stop bar rotationally mounted about the rotation axis and a driving rod connected to the stop bar. The stop bar has a portion positioned within the pivot path of the pivot member which is offset from the rotation axis and a driving rod is positioned to engage the engagement surface when the pivot member strikes the stop bar.

The medical device can include a ring gear positioned cylindrically and concentric to the rotation axis. The driving mechanism can include a stop bar with a toothed edge positioned to engage the ring gear. The driving mechanism is positioned to engage the pivot member and ring gear. The pivot member is pivotable through a range bounded by the stop bar such that during pivotal rotation of the pivot member, abutment of the pivot member against stop bar causes the toothed edge to move along the ring gear.

The medical device can include a diametric permanent magnet having a first magnetic field with poles aligned substantially perpendicular to the pivot axis. Application of electric current to the coil creates a second magnetic field with poles aligned substantially along the rotation axis such that interaction between the first and second magnetic fields creates the torque.

The medical device can include a bias member. The pivot member can include the transducer. The bias member can be positioned to apply a bias member force to the transducer which biases the transducer to a neutral position about the pivot axis and relative to the pivot mechanism. The torque is dependent upon the electric current to the coil such that when the torque is insufficient to overcome the bias member force, the bias member force returns the transducer to the neutral position. The bias member can be a conductor configured for carrying signals from the transducer.

The transducer is movable throughout a range which defines a viewing window extending from the transducer. The medical device can include an opaque feature positioned within the viewing window such that the opaque feature provides angular positional information about the pivot member.

The medical device can include a tubular member for housing the transducer, driving mechanism, and pivot mechanism. The tubular member has a distal chamber defined at least in part by a wall portion of the tubular member. The distal chamber houses at least the transducer and the medium. The wall portion and the medium have similar acoustic impedance to the part of the body into which the tubular member is inserted so that reflection of ultrasound at the boundary of the medium and the wall portion and at the boundary of the wall portion and the body environment is reduced to a level acceptable for imaging through the boundary. The tubular member can be a catheter.

The medical device can include a transducer for transmitting and/or receiving ultrasound signals, and a pivot mechanism rotatably mounted about the rotation axis. Also included is a pivot member pivotally mounted to the pivot mechanism about a pivot axis substantially perpendicular to the rotation axis. An engagement surface is positioned cylindrically and concentric to the rotation axis. A driving mechanism is positioned to engage the pivot member and engagement surface. The pivot member is pivotable through a range bounded by the driving mechanism such that during pivotal rotation of the pivot member, abutment of the pivot member against the driving mechanism moves the driving mechanism to engage the engagement surface to create a reactionary force which causes the pivot mechanism to rotate about the rotation axis. The pivot member can include a magnetic layer and the transducer. A coil can be positioned concentric to and along the rotation axis. The coil can include a plurality of electrically conductive windings such that application of electric current to the coil creates a torque on the pivot member about the pivot axis.

The medical device can include one or more sensors for sensing the position and/or movement of the transducer, and/or a portion supporting or coupled to the transducer (e.g., the pivot mechanism, pivot member, or magnetic layer), about the pivot axis and/or the rotation axis. A data processing system can use the sensor data to calculate the speed and/or position of the transducer and correlate that sensor data with the data or signals received by the transducer so as to generate a graphic display (e.g., an IVUS image). The same or a different data processing system can also use the sensor data in controlling the voltage applied to the coil. For example, a feedback loop can increase or decrease the voltage of coil so as to adjust the speed at which the pivot member and transducer pivot.

Further forms, objects, features, aspects, benefits, advantages, and embodiments of the concepts will become apparent from a detailed description and drawings provided herewith.

BRIEF DESCRIPTION OF THE DRAWINGS

FIG. 4 is an illustrative partial side view of a pivoting transducer illustrating operation in conjunction with a drive signal.

FIG. 5 is an illustrative partial side view of a pivoting transducer illustrating operation in conjunction with a drive signal having a DC offset component.

FIG. 6 is an illustrative partial side view of a pivoting transducer illustrating operation in conjunction with a drive signal having a DC offset component opposite to that shown in FIG. 5.

DESCRIPTION OF THE SELECTED EMBODIMENTS

Figure 1:
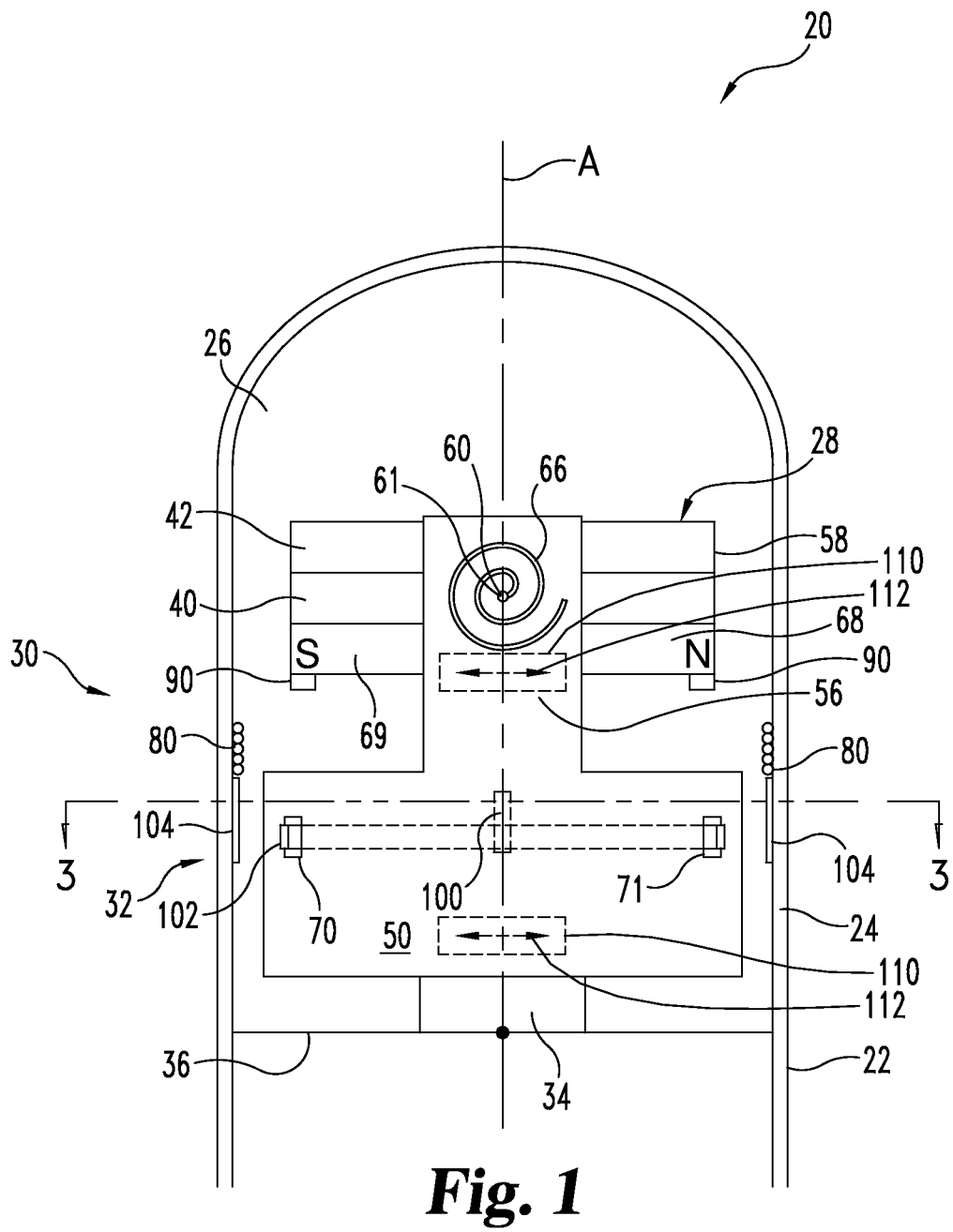
FIG. 1 is an illustrative side view of a medical device showing a pivot mechanism.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. One or more embodiments are shown and described in detail, although it will be apparent to those skilled in the relevant art that some features that are less relevant may not be shown for the sake of clarity.

Referring now generally to the drawings, there are shown exemplary embodiments of a device 20 for internal ultrasound procedures. Such devices may be diagnostic or therapeutic (including interventional) in application, and include devices inserted percutaneously, subcutaneously or endoluminally into the patient. Device 20 can be used with a system which includes a console (not shown) for processing data or signals received from an ultrasound transducer. The ultrasound console can be a type which is generally used for medical ultrasonic imaging, e.g. generally including control devices usable by a physician and a graphic display which displays graphical images obtained during an ultrasound procedure. Device 20 can be used for obtaining images at various locations of a body such as a blood vessel, urethra, ureter, vagina, rectum, throat, ear, or through an artificial tract (or lumen) by percutaneous puncture for example. The console portion can be connected to commercially-available ultrasound probes or catheters with compatible pinout, or other medical devices which are configured for endoluminal procedures. Device 20 is capable of transmitting and receiving ultrasound signals and then communicating data obtained from ultrasound signals to the console.

In the embodiment shown schematically in FIG. 1, device 20 includes a catheter 22 or other flexible elongated or tubular member having a wall 24 defining an internal chamber 26, within which is included a transducer 28, a pivot mechanism 30, a driving mechanism 32, and a coil 80. Catheter 22 is sized and configured for insertion into and/or travel along bodily orifices or lumens. As will be discussed further below, pivot mechanism 30 allows transducer 28 to be turned around a rotation axis (axis A) of device 20 as well as pivoted around a pivot axis substantially perpendicular to the rotation axis, allowing the direction of ultrasound emission and reception to extend forward (axially relative to the rotation axis) and laterally (radially relative to the rotation axis). In the illustrated embodiments, the rotation axis is the longitudinal axis (i.e. extending axially through catheter 22) of device 20, and the pivot axis is a lateral axis (e.g. perpendicular to the longitudinal axis). Transducer 28 in conjunction with driving mechanism 32 and pivot mechanism 30 is capable of transmitting and receiving ultrasound signals in a variety of directions or orientations which are passed along data signal communication lines between transducer 28 and the ultrasound console.

Catheter 22 in the illustrated embodiment is an elongated device of plastic or other sturdy flexible material. Catheter 22 includes a control end which during use is nearest to the user and an application end which during use is nearest to the user's point of interest. The terms "control" and "application" are used throughout this description to describe these positional orientations. Wall 24 surrounds chamber 26, which is at or near the application end of device 20 in the illustrated embodiment. The control end of wall 24 and/or catheter 22 may extend outside of the patient during use, or may attach to another piece that extends outside the patient, and may end in a handle or other operating portion for maneuvering catheter 22.

Catheter 22 has at least a portion that presents a minimal barrier to the passage of ultrasound signals so that ultrasound images of surrounding matter (e.g. tissue(s) or implant(s)) may be reasonably acquired through the barrier. Catheter 22 has a portion surrounding device 20 that is constructed of a material which is substantially echolucent (i.e. having small ultrasound attenuation, or having a small difference in acoustic impedance with the surrounding environment) when placed in the surrounding working environment, such that it acts as an acoustic window which allows passage of ultrasound signals with minimal reflection. It will be understood that only the application end of catheter 22 (e.g. wall 24) need be acoustically transparent, but more or all of catheter 22 may be made of the same material as wall 24 in some embodiments. For example, when used within a blood vessel containing body tissues and blood, it is preferable for catheter 22 to be constructed of a material which is structurally rigid and which has acoustic impedance similar to that of body fluids such as blood. Possible materials could include, for example, a polymer material such as high density polyethelene, polymethylpentene (PMP), or acrylonitrile butadiene styrene (ABS). It has been determined that in some cases the thickness of at least the portion of catheter 22 which serves as the viewing window can be approximately N/2 (where N is a positive integer) of the wavelength corresponding to the center frequency of the ultrasound signal.

Particular embodiments of catheter 22 or at least chamber 26 are cylindrical, and are sized for insertion into and passage through body conduits, such as insertion into the femoral artery and passage through it toward the heart. Wall 24 may have a port or other feature to allow injection of fluid (e.g. saline, oils, or alcohols) into chamber 26 to give chamber 26 ultrasound characteristics similar or substantially identical to that of wall 24 and the surrounding bodily environment (e.g. the blood stream). A sealing member 36 can be placed on the control side of pivot mechanism 30 and transducer 28 or the portion of chamber 26 containing transducer 28 and a fluid, in the illustrated embodiments.

Figure 2:
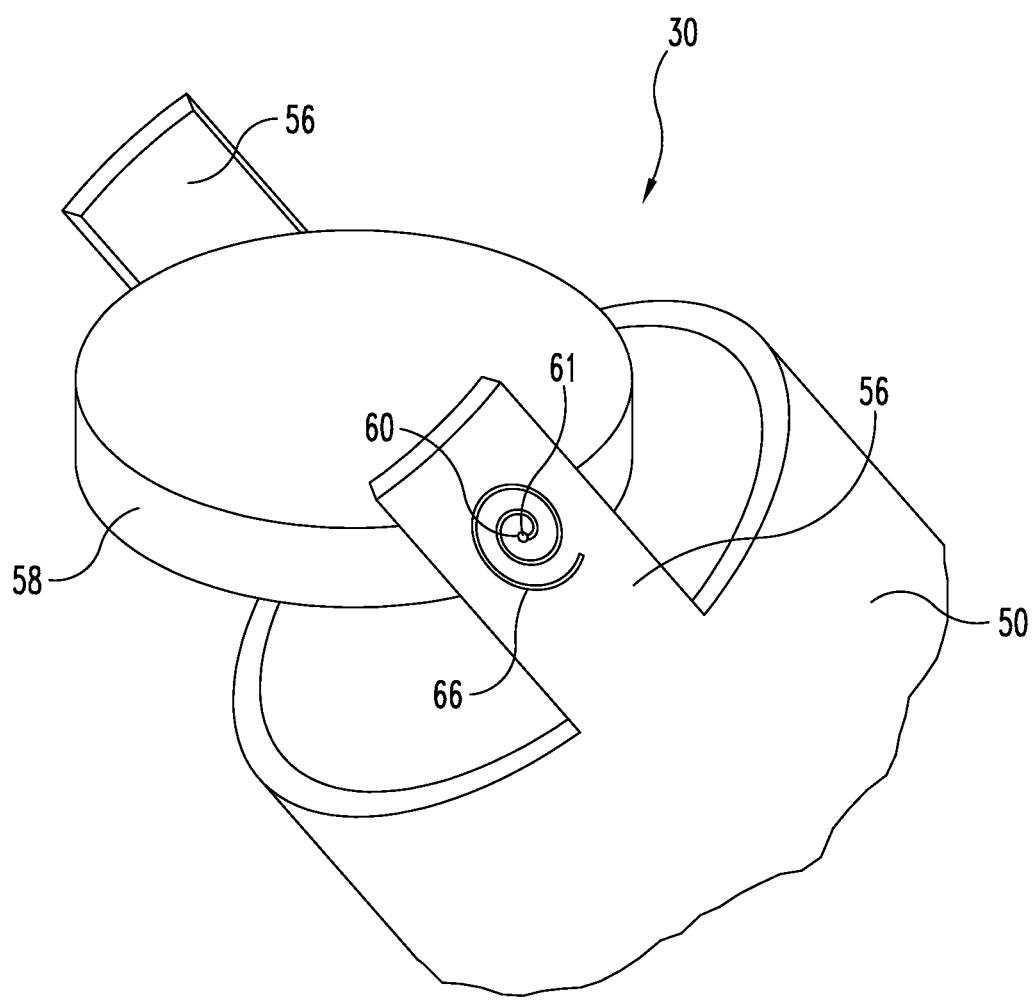
FIG. 2 is an illustrative partial perspective view of the pivot mechanism of FIG. 1.

Transducer 28 is mounted in pivot mechanism 30 to permit transducer 28 to turn around the rotation axis as well as pivot around the pivot axis. In the illustrated embodiments (e.g., FIG. 2), pivot mechanism 30 is a two-axis gimbal or gimbal-type mounting (or yoke), having a base 50 and matching arms 56 extending from base 50. Base 50 and arms 56 can be constructed from a generally cylindrical object having a lumen extending therethrough and wherein arms 56 are constructed by cutting out a portion of the cylindrical object. Alternatively, a base 50 and arms 56 may be separate pieces which are attached by glue, weld, friction fit, or other suitable means. Base 50 is attached to a bearing 34, so that pivot mechanism 30 is rotatable about the rotation axis. In some embodiments, bearing 34 has a lumen extending therethrough, which permits electrical conductors, guidewires, or other structures to pass through the bearing. Base 50 includes slots 70, 71, which are cutouts or holes in the wall of base 50. A pivot member 58 is mounted to arms 56 via holes 60 in arms 56. Pivot member 58 in the illustrated embodiment is a circular shaped disk having shafts 61 that fit into holes 60 and act as an axle so that pivot member 58 can pivot around the pivot axis. Other gimbal structures could be used which provide pivoting (or elevational) rotational motion to the transducer, examples of which are explained in U.S. Patent App. Ser. No. 61/713,172

(entitled "Devices and Methods for Three-Dimensional Internal Ultrasound Usage") and U.S. Patent App. Ser. No. 61/748,774 (entitled "Ultrasound Transducer Direction Control"), which are incorporated herein by reference in their entirety.

One or more bias members 66 bias pivot member 58 to a particular initial resting or neutral position. In the illustrated embodiment, bias member 66 is a torsion spring connected to an arm 56 at or toward one end, and to a shaft 61 or pivot member 58 at the other end (e.g. by inserting an end of bias member 66 into a groove in shaft 61). The torsion spring is a helically shaped spring in a particular embodiment, although other spring types are suitable. A second bias member 66 (not shown) may be similarly attached to the other arm 56 and shaft 61 or pivot member 58. In the FIG. 1 embodiment, in the neutral position, transducer 28 is oriented so that transducer 28 has a viewing angle which is substantially aligned with the rotation axis, e.g. with pivot member 58 generally normal to the rotation axis. In other embodiments, the neutral position can be different (e.g. with the viewing angle substantially perpendicular to the rotation axis).

As previously noted, in the illustrated embodiment, transducer 28 is mounted to pivot member 58. Pivot member 58 also includes a magnetic layer 68. Transducer 28 is indicated schematically in the drawings. The term "transducer" should be understood to include an assembly of two or more parts as well as a single piece. It will further be understood that "transducer" as used herein includes devices that transmit ultrasound signals (i.e. transform an electrical (RF) signal to ultrasound), receive ultrasound signals (i.e. transform ultrasound to an electrical (RF) signal), or both. If multiple transducers or pieces are provided, transmission of ultrasound may occur at one and reception at another. Transducer(s) as described herein may have one or more piezoelectric elements as respective transducers, and may operate in combination with other transducers within or outside the body. As examples, "transducer" as used herein includes a single element transducer on a rotating and pivoting member or a one-dimensional array of elements on a rotating and pivoting member.

An exemplary transducer 28 includes a body or backing 40 with at least one ultrasound element 42 attached to one side of backing 40, and one or more clamping rings. Transducer 28 can include a matching layer (not shown) attached to one side of element 42. Element 42 in this embodiment is a piezoelectric element which has the ability to convert electrical energy into sound waves and sound waves into electrical energy. The positioning of element 42 as indicated, on a side of backing 40, results in a directed ultrasound beam direction. Backing 40 may be substantially opaque to ultrasound signals, so that such signals are effectively only projected outward from element 42, e.g. to one side or in a limited angular range radially (relative to the pivot axis) from backing 40. The matching layer has acoustic impedance generally between that of element 42 and the medium surrounding transducer 28 in order to minimize mismatched acoustic impedance between transducer 28 and the medium surrounding transducer 28. Transducer 28, as discussed, can be a single element transducer which is capable of sending and receiving ultrasound waves in a range of frequencies which are typically used in medical ultrasound procedures, such as, for example, in the range from 20 KHz to 100 MHz. In some examples, transducer 28 can include a linear array of elements extending along the rotation axis. Clamping rings have been determined to improve efficiency and add mechanical stability to transducer 28.

Magnetic layer 68 is positioned adjacent to or integral with backing 40 in the illustrated embodiment. Magnetic layer 68 may be a permanent magnet attached to transducer 28 adjacent to backing 40. Alternatively, magnetic layer 68 could be incorporated into a transducer housing. In other embodiments, a magnet or magnetic material may be integrated with the backing layer as a composite or other method. In the FIG. 1 embodiment, magnetic layer 68 is a permanent diametric magnet 69 having a generally cylindrical shape with the poles aligned in the radial direction, in which a pole axis running through the north and south poles is generally perpendicular to the pivot axis.

In particular embodiments, pivot member 58 is a body, base or substrate on which backing 40 of transducer 28 (or transducer 28 itself) is fixed. In other embodiments, backing 40 may include shafts 61 so as to become the pivot member in pivot mechanism 30, or a separate axle may be provided with pivot mechanism 30 to which backing 40 or magnetic layer 68 is directly or indirectly fixed. Pivot mechanism 30 permits transducer 28 to turn around the rotation axis, via bearing 34 and driving mechanism 32, and to turn transducer 28 about the pivot axis at the same time, via pulling or pushing force on magnetic layer 68 to move it around the pivot axis. Pivot member 58 is thus able to rotate about both the pivot axis and the rotation axis simultaneously.

Coil 80 is a conductor which is wrapped or coiled multiple times about the rotation axis. In the embodiment of FIG. 1, coil 80 is positioned in the axial direction (relative to the rotation axis) on the control side of transducer 28. Coil 80 is positioned adjacent to wall 24 of catheter 22. In some embodiments, coil 80 can be positioned within chamber 26 and positioned adjacent to or abutting the inside surface of wall 24. In other embodiments, coil 80 can be positioned adjacent to or abutting the outside surface of wall 24. In other embodiments, coil 80 can be integrated into wall 24 of catheter 22. In still other embodiments, coil 80 can be positioned about a tubular sheath (not shown) which is positioned within catheter 22 and surrounds at least a portion of pivot mechanism 30. In this way, catheter 22 or a sheath provide structural support for coil 80. In other embodiments, coil 80 can be positioned closer to or further from transducer 28. Coil 80 has multiple windings which are positioned concentric to the rotation axis. Coil 80 has at least one end which is connected to a power source (not shown) as by a conductor leading to or toward the operating end of device 20. In some embodiments, coil 80 has two ends which are connected to the power source by conductors leading to or toward the operating end of device 20. In other embodiments, a single conductor conducts a signal toward the operating end of device 20, and a conductive fluid within chamber 26 provides a second conductive path. The power source can be positioned within or without catheter 22 (e.g., integrated with the console). The power source applies an electric current to coil 80.

Figure 3:
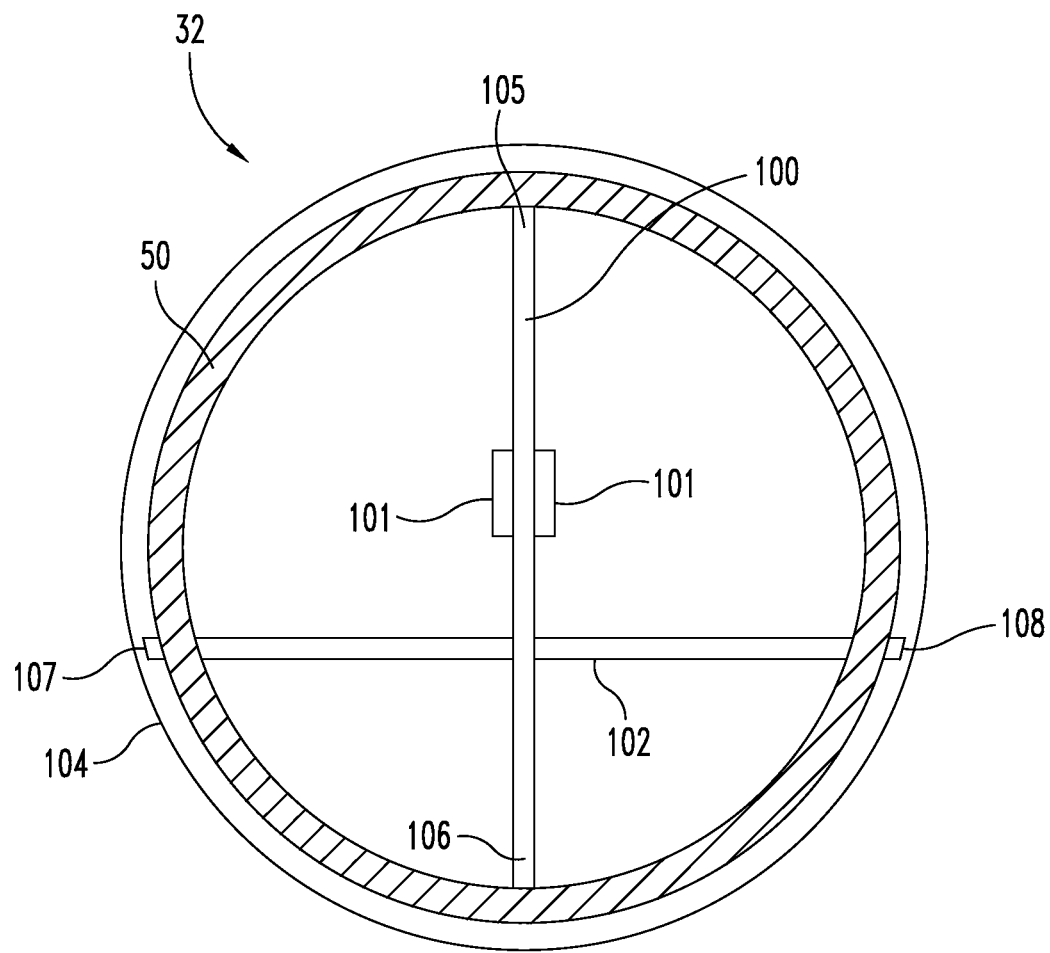
FIG. 3 is an illustrative top cross-sectional view of the pivot mechanism of FIG. 1 showing a driving mechanism.

In the illustrated embodiment, driving mechanism 32 includes a stop bar 100, a driving rod 102, and a friction ring 104. In the illustrated embodiment, stop bar 100 is an elongated elastic bar such as a leaf spring constructed of a material (e.g. aluminum, or various polymers) having sufficient elasticity which allows it to flex from a resting position when impacted and then resume the resting position. Stop bar 100 is positioned within the pivotal path of pivot member 58. Stop bar 100 is anchored at one or both ends to base 50 (FIG. 3). In the FIG. 3 embodiment, end 105 is anchored to base 50 and end 106 is free to move circumferentially relative to base 50. In one embodiment, end 106 can be positioned in a cutout or slot within base 50 such that flexing of stop bar 100 causes end 106 to slide within the slot yet maintain a relatively fixed circumferential position relative to base 50. In other embodiments, both ends 105, 106 may be anchored to base 50. Stop bar 100 may include a bumper(s) 101 attached at the center (or substantially along the rotation axis) of stop bar 100. Alternatively, bumper 101 may be integral to stop bar 100.

Driving rod 102 is an elongated bar attached to stop bar 100. The attachment may be by glue, weld, friction fit, or other suitable method. Driving rod 102 is constructed of a material which is generally rigid. Driving rod 102 extends perpendicularly from stop bar 100 and has ends 107, 108 which extend or are extendable through slots 70, 71 in base 50. Ends 107, 108 are configured to engage friction ring 104. Friction ring 104 (or engagement surface) is a circumferential band positioned circumferentially near base 50. In some embodiments, friction ring 104 is the inside surface of wall 24 of catheter 22. In other embodiments, friction ring 104 may include a band of rubber material, or other material which has grooves, slots, or steps positioned at the radially inward-most surface of friction ring 104. In some embodiments, friction ring 104 is positioned circumferentially along the inside surface of wall 24 of catheter 22. In other embodiments, friction ring 104 can be positioned about a sheath which is separate from wall 24. In still further embodiments, friction ring 104 may include features which are molded or cut into the inner surface of wall 24. Friction ring 104 is positioned in the axial direction (relative to the rotation axis) adjacent to driving rod 102 and ends 107, 108.

Coil 80 is positioned such that when energized, coil 80 creates a magnetic field with poles aligned substantially with the rotation axis. In the FIG. 1 embodiment, magnetic layer 68 has poles which are symmetrically arranged perpendicularly about the pivot axis. A magnetic field produced by coil 80 has a pole (e.g. north) closest to pivot member 58 which attracts the opposite pole (e.g. south) of magnetic layer 68. The force of attraction between the two poles applies a torque to pivot member 58. When the torque is large enough to overcome the spring force of bias members 66, pivot member 58 rotates about the pivot axis from the neutral position. The magnitude of the torque can be varied by altering the magnitude of the current applied to coil 80, and the direction of the torque can be changed by reversing the direction of the current and thus the polarity of coil 80.

At or near the end of its pivot range, pivot member 58 strikes stop bar 100 which is positioned within the pivotal path of pivot member 58. In this way, pivot member 58 is free to rotate through a range of about 180 degrees, or about 90 degrees in either direction from the neutral position until a portion of it strikes stop bar 100. Optional bumpers 90 are positioned on pivot member 58 adjacent to magnetic layer 68 and are positioned to engage bumpers 101. In that way, stop bar 100 receives kinetic energy from pivot member 58 and translates it to driving rod 102. The impact from pivot member 58 causes stop bar 100 to flex from its neutral (or resting) central position. Upon flexing, stop bar 100 causes driving rod 102 to move in a longitudinal direction relative to driving rod 102 (or transverse direction relative to stop bar 100). One of the ends 107, 108 of driving rod 102 impacts friction ring 104 and the reactionary force is transferred through stop bar 100 to its anchor point(s) on base 50 creating a torque which causes base 50 to rotate a particular distance (or defined angle) about the rotation axis relative to friction ring 104 and likewise catheter 22.

The elastic properties of stop bar 100 cause stop bar 100 to return to its neutral position. Similarly, the current applied to coil 80 can be reduced or eliminated so that the spring force of bias members 66 overcomes the torque of the magnetic fields in order to return pivot member 58 to the neutral position. Alternatively or additionally, the current may be reversed to create an opposing magnetic field which creates a torque which works in conjunction with the spring force from bias members 66 to return pivot member 58 to or toward the resting position. Once in the resting position, an opposite (or appropriate) current can be applied to coil 80 which causes pivot member 58 to again rotate about the pivot axis.

It is advantageous for pivot member 58 to alternatingly undergo a driving pivot stroke and a non-driving pivot stroke. The driving pivot stroke has a torque which is larger than the non-driving pivot stroke. The driving pivot stroke has a torque which is large enough to cause pivot member 58 to impact stop bar 100 with sufficient force to cause driving rod 102 to impact friction ring 104 and cause rotational motion of pivot mechanism 30 about the rotation axis. The non-driving pivot stroke has a torque which is sufficient to cause pivot member 58 to rotate through its complete pivotal range up to and optionally including impacting stop bar 100. However, the torque of the non-driving pivot stroke is insufficient to cause driving rod 102 to impact friction ring 104. Alternatively, the torque of the non-driving pivot stroke may be sufficient to cause driving rod 102 to impact friction ring 104, but the torque is insufficient to cause rotational motion of pivot mechanism 30 about the rotation axis. By continuously providing alternating driving pivot strokes and non-driving pivot strokes, an incremental unidirectional rotation of pivot mechanism 30 about the rotation axis is achieved.

Various drive signals can be applied to coil 80 in order to achieve and control the two-axis motion described herein. For example, a drive signal can include an alternating current applied to coil 80 to achieve reciprocating pivotal motion of pivot member 58. The alternating current repeatedly changes direction which changes the polarity of the magnetic field produced by coil 80. Correspondingly, the torque applied to pivot member 58 is alternated repeatedly, and pivot member 58 is caused to reciprocate pivotally about the pivot axis. In this case, the pivot member strikes the stop bar with the same force at both ends of its pivotal range (FIG. 4), and no continuous unidirectional rotation occurs. In some embodiments, a direct current (or DC) bias signal is added to the alternating current signal (illustrated in FIGS. 4-6). The DC bias signal causes the opposing magnitudes of the AC signal to shift relative to a symmetrically centered, neutral axis (FIGS. 5, 6). The drive signal then causes a larger torque force (indicated by the bold arrows in FIGS. 5, 6) in one direction relative to the opposite direction. The larger torque force is transmitted to stop bar 100 at one end of the pivotal range of pivot member 58 while a smaller torque force is transmitted to stop bar 100 at the other end of the pivotal range of pivot member 58. For example, the signal shown in FIG. 5 has a DC signal which causes pivot member 58 to strike stop bar 100 with greater force in a clockwise direction than in the counterclockwise direction. Similarly, the signal shown in FIG. 6 has an opposite DC signal which causes pivot member 58 to strike stop bar 100 with greater force in a counterclockwise direction than in the clockwise direction. In this way, the rotational direction of pivot mechanism 30 about the rotation axis can be controlled and altered by changing and/or reversing a DC component of the drive signal. Other drive signals to accomplish similar results may be used.

In some instances, device 20 includes a sensor that senses a position and/or movement of transducer 28, and/or a portion supporting or coupled to transducer 28 (e.g., the pivot mechanism, pivot member 58, or magnetic layer 68), about the pivot axis (e.g., shaft 61). Similarly, one or more sensors may be included in device 20 to detect the rotational position or movement of transducer 28, and/or a portion supporting or coupled to transducer 28, about the rotation axis (axis A). The sensor outputs sensor data that is communicated to a data processing system (not illustrated) which, in turn, can process the sensor data to calculate the speed (e.g., angular velocity) and/or position (e.g., angular orientation) of transducer about the pivot axis and/or the rotation axis. The speed and/or position calculation can then be paired with the data or signals received from the transducer so as to generate a graphical image and/or so as to adjust the voltage applied to coils 80. For example, the data processing system can calculate or measure the time between stop bar 100 strikes and, using the known parameter of the degrees of rotation between strikes, calculate or look up from a lookup table the rotational speed of the transducer. This rotational speed may then be used to determine the position (e.g., angular orientation) of the transducer at one or more points in time. When the signals received by the transducer are correlated to the position of the transducer at the time at which that signal was received, a graphical image (e.g., 2D or 3D) may be generated. Alternatively or additionally, the sensor data may be incorporated into a feedback loop that adjusts the magnitude and/or frequency of the AC or DC signal applied to coil 80. For example, the sensor data may be used to increase/decrease the voltage and/or frequency of electrical energy applied to coil 80 so as to increase/decrease the rotational velocity of the transducer. Increasing/decreasing the angular velocity (in pivoting and/or rotational movement) of the transducer can be used to increase/decrease the refresh rate and decrease/increase the resolution of the graphical image for a given transducer frequency.

The sensor may comprise any sensor suitable for sensing the position and/or movement of the transducer and/or a portion supporting or coupled to the transducer (e.g., the pivot mechanism, pivot member, or magnetic layer). For example, sensor 110 may comprise a sensor that varies its output in response to the magnetic field of the magnetic layer (e.g., a Hall Effect sensor that detects a magnetic pole of magnetic layer 68 when the magnetic pole and the sensor are in proximity to one another). As another example, sensor 110 may comprise an electrical contact or switch that, when contacted by a portion of pivot member 58 such as bumper 90, closes an electrical circuit. Alternatively or additionally, sensor 110 may include an encoder (linear or rotary), a potentiometer, and/or an accelerometer, just to name a few non-limiting examples.

The sensor may be positioned in a number of locations within device 20. In many instances, the position of the sensor will be dependent on the type of sensor and the position or movement being sensed. For example, one or more Hall Effect sensors may be positioned on arm 56 and/or on base 50 to sense the position of the magnetic layer about the pivot axis. In some embodiments, a Hall Effect sensor is positioned underneath the pivoting transducer on base 50 near the center of the catheter (e.g., close to stop bar 100).

To reduce interference from the magnetic field generated by coil 80, the sensor may be a directional sensor with the direction of sensitivity (indicated by arrows 112) oriented transverse to the magnetic field lines created by coil 80. Preferably, the direction of sensitivity of sensor is orthogonal to the field lines created by coil 80. For instance, a Hall Effect sensor can be positioned with the direction of sensitivity either in a tangential direction to the coil current or extending radially from the center of the loop formed by coil 80 (e.g., the center of the catheter bore).

As additional examples, an electrical contact sensor can be positioned on stop bar 100, such as on bumper 101, to detect the contact of bumper 90 with bumper 101. Additionally or alternatively, a rotary encoder can be positioned adjacent to shaft 61 to detect rotation about the pivot axis and/or adjacent to bearing 34 to detect rotation about the rotation axis. In some instances, the transducer can be used to detect the impact of the pivot member and the stop bar. For example, a transducer having one or more piezoelectric elements can sense the vibration from when the pivot member strikes the stop bar.

In some embodiments, one or more acoustically opaque or attenuating features may be placed in the viewing window such that the ultrasound field crosses the opaque feature at one or both ends of the pivoting range of transducer 28. Stop bar 100 may be positioned and/or configured such that transducer 28 stops generally at a moment when the ultrasound field crosses the acoustically opaque feature. The acoustically opaque feature may be added to or integrated with a catheter 22, examples of which are discussed and shown in U.S. Application Ser. No. 61/713,142, entitled "Feedback/Registration Mechanism for Ultrasound Devices," which is incorporated by reference herein in its entirety.

Transducer 28 is electronically connected to a power source and to an imaging system via signal carriers. Bias members 66 can be constructed of a conductive material and be linked to transducer 28 and/or the console or power source to carry electrical signals to and/or from transducer 28. In particular embodiments, bias members 66 provide a conduction path from transducer 28 to conductors positioned along arms 56. Alternative to or in conjunction with bias members 66, other signal carriers could be positioned to carry a signal from transducer 28 toward the console side of device 20. Other examples of signal carriers include conductors (e.g. wires or cables) along wall 24, through a central lumen of bearing 34, via slip ring connections, and/or via metallic film(s) along wall 24. Examples are discussed and shown in U.S. Application Ser. No. 61/714,275 (entitled "Internal Transducer Assembly with Slip Ring"), which is incorporated by reference herein in its entirety.

A portion of chamber 26 immediately surrounding transducer 28 extending towards the application end of catheter 22 can be completely filled with a fluid or other substance having acoustic impedance similar to that of blood or tissue, such as saline, oils (e.g. mineral oil or castor oil), or mixed alcohol. Sealing member 36 provides a fluid seal between the chamber surrounding transducer 28 and the control side of catheter 22. The substance preferably minimizes friction acting against transducer 28 during rotation. Through use of the substance, acoustic matching can be achieved between body fluids, catheter 22, and the medium immediately surrounding transducer 28. Acoustic matching ensures that minimal signal losses occur when transmitting and receiving ultrasound signals between transducer 28 and body tissue which enhances the clarity of the resulting image. The fluid can be added to device 20 during manufacture, or alternatively could be added prior to use. When the transducer is sealed and the coupling fluid is placed into the chamber during manufacture, long term contact with the parts necessitates a non-corrosive fluid such as mineral oil or castor oil in order to preserve the shelf life of the product. Preferably, the oil is bio-compatible, acoustically transparent, and has low viscosity. Alternatively, a fluid communication port (not shown) may be positioned or creatable within the catheter or through the catheter wall to allow access for adding a fluid. In that case a corrosive fluid may be added at the time of deployment of device 20. Corrosive fluids such as water, saline, and alcohol typically have more favorable combinations of bio-compatibility, acoustic transparency and viscosity.

An exemplary use of device 20 will now be given. Device 20 is prepared (e.g. by injecting a fluid into chamber 26, if not already present) and inserted into the body of a patient and maneuvered to a desired location, e.g. in a particular blood vessel. Transducer 28 may be operated during travel to the desired location, as transducer 28 has a forward neutral position and can be pivoted through use of coil 80. Throughout placement and at a desired imaging location, coil 80 can be energized in order to pivot transducer 28 about the pivot axis to shift the ultrasound field forward and/or laterally. Additionally transducer 28 can be rotated about the rotation axis via a driving mechanism 32 to provide images of tissue(s) or other matter around device 20. Correspondingly, transducer 28 rotates about one or both the rotation axis and the pivot axis. In this way, device 20 provides an ultrasound signal sweep or field that not only turns around the rotation axis of device 20 but also around the pivot axis in order to look forward and/or laterally of a particular position of transducer 28.

When an ultrasound signal is transmitted, the ultrasound signal passes across wall 24 of catheter 22 until it encounters an acoustic impedance boundary (e.g. body tissue, plaque, medical implant, or other material which has acoustic impedance sufficiently different from bodily fluids or other surrounding material) such that the ultrasound signal is at least partially reflected at the boundary. At least a portion of the ultrasound signal is reflected back towards transducer 28. One or more electrical signals representing reflected ultrasound received at transducer 28 are sent from transducer 28 via a conduction pathway to the ultrasound console, for imaging and/or other data display to the physician. Simultaneously or subsequently transducer 28 continues to transmit further ultrasound signals and the process is repeated, continuously in certain embodiments over a desired period of time.

Figure 7:
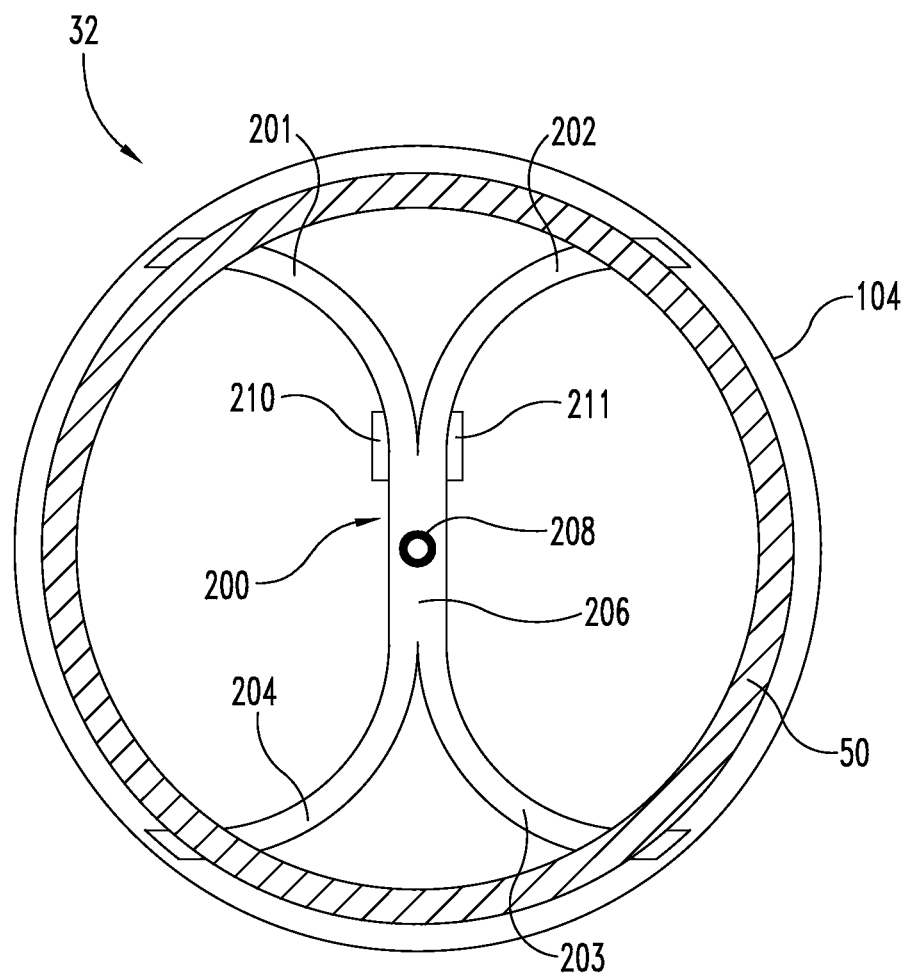
FIG. 7 is an illustrative top cross-sectional view of the pivot mechanism of FIG. 1 showing an alternative driving mechanism.

An alternative embodiment of driving mechanism 32 is depicted in FIG. 7. In that embodiment, driving mechanism 32 includes a stop bar 200, driving rods 201, 202, 203, 204, and friction ring 104. In the illustrated embodiment, stop bar 200 has a central portion 206. The driving rods 201, 202, 203, 204 extend from the central portion 206 generally in four separate directions as shown in FIG. 7. The ends of driving rods 201, 202, 203, 204 extend through slots or holes in the circumferential wall of base 50 towards friction ring 104. Central portion 206 has a hole 208 which is adapted to provide a rotational mount, wherein stop bar 200 is rotationally mounted relative to base 50 substantially along the rotation axis. The mount can be integrated into bearing 34 in a way that provides rotational motion independent of rotational motion of pivot mechanism 30. Positioned on central portion 206 are bumpers 210, 211 which are generally offset from the rotation axis. Central portion 206 and more specifically bumpers 210, 211 are positioned within the pivot path of pivot member 58, and bumpers 210, 211 are positioned to engage bumpers 90 on pivot member 58 as pivot member 58 pivots about the pivot axis in this configuration. Bumpers 90 can be configured to extend beyond the outer circumferential surface of pivot member 58 so as to be in a proper position to impact bumpers 210, 211 at a position offset from the rotation axis. Alternatively, bumpers 210, 211 and/or bumpers 90 can be configured to extend a sufficient distance away from their respective mounting surfaces so that pivot member 58 does not physically impede rotation of central portion 206 about the rotation axis.

An impact from one of bumpers 90 on one of bumpers 210, 211 causes a torque on central portion 206 which causes central portion 206 to rotate about hole 208 or the rotation axis (e.g. in a clockwise direction relative to FIG. 7). Two of the driving rods impact friction ring 104 (e.g. driving rods 202, 204) when pivot member 58 strikes stop bar 200. The impact causes one or more of driving rods 201, 202, 203, 204 to partially abut against the edges or inside surfaces of the slots in the wall of base 50. The combination of driving rods impacting friction ring 104 and the edges or inside surfaces of the slots in the wall of base 50 causes a torque on pivot mechanism 30 which causes it to rotate a certain distance about the rotation axis.

Figure 8:
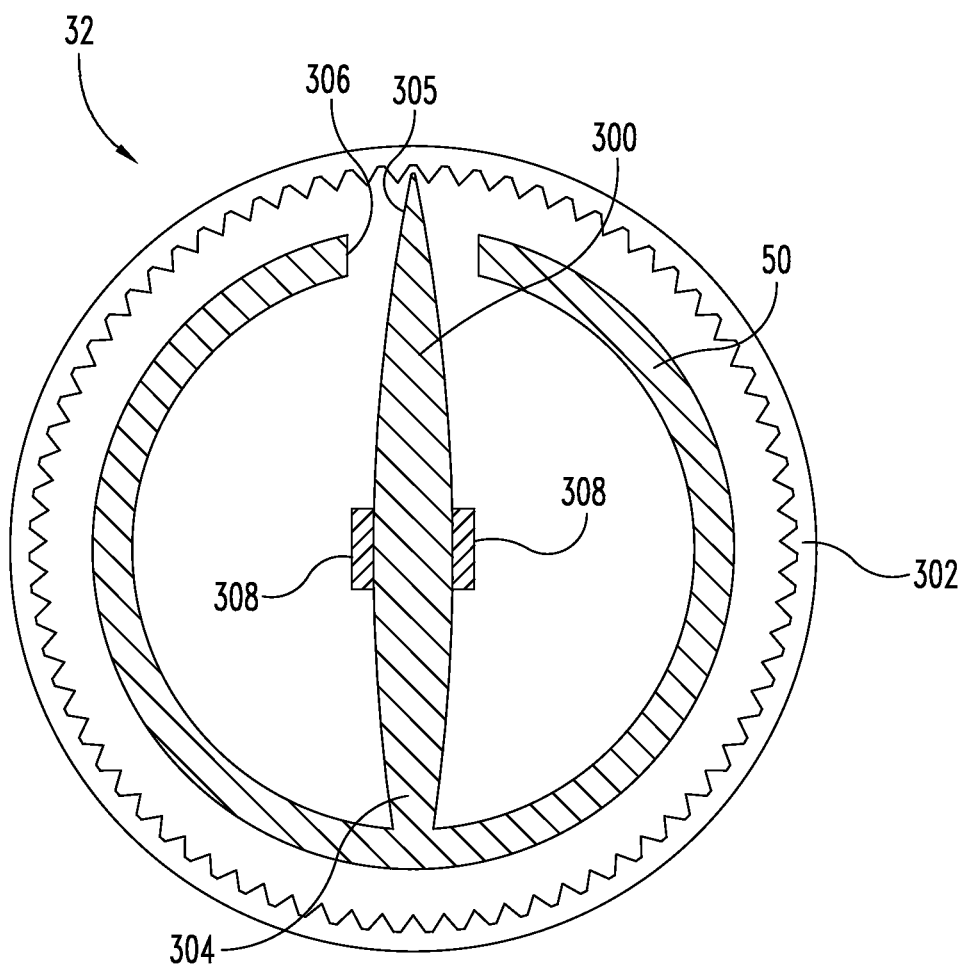
FIG. 8 is an illustrative top cross-sectional view of the pivot mechanism of FIG. 1 showing an alternative driving mechanism.

An alternative embodiment of driving mechanism 32 is depicted in FIG. 8. In that embodiment, driving mechanism 32 includes a stop bar 300 and ring gear 302. Stop bar 300 includes end 304 and edge 305. Stop bar 300 can be integral to base 54 fixedly attached to base 50 at end 304. Stop bar 300 is constructed of a flexible or resilient material (e.g. various metals or polymers) that allows edge 305 to flex from a neutral position (or central, or resting) in a generally circumferential direction about a pivot point which is generally end 304. Edge 305 extends through opening 306 in base 50. Ring gear 302 is a generally internal gear which is integrated with or separately attached to wall 24 of catheter 22. Ring gear 302 has inward facing teeth which are configured to engage with edge 305. Edge 305 is structured as a toothed edge (or knife edge) that engages the inward facing teeth of ring gear 302. Bumpers 308 are positioned on stop bar 300 in the pivotal path of pivot element 58, and more specifically in the pivotal path of bumpers 90 on pivot element 58.

During operation (more specifically during a driving pivot stroke) when pivot member 58 strikes stop bar 300, stop bar 300 receives kinetic energy from pivot member 58 and flexes about end 304. Edge 305 shifts to a point between the next adjacent teeth, and a reactionary force is transferred through stop bar 300 to end 304 and subsequently to base 50 causing base 50 to rotate a defined distance (or defined angle) about the rotation axis. During a subsequent non-driving pivot stroke, pivot member 58 may strike stop bar 300 but the force is insufficient to cause edge 305 to shift to a point between the next adjacent teeth.

Figure 9:
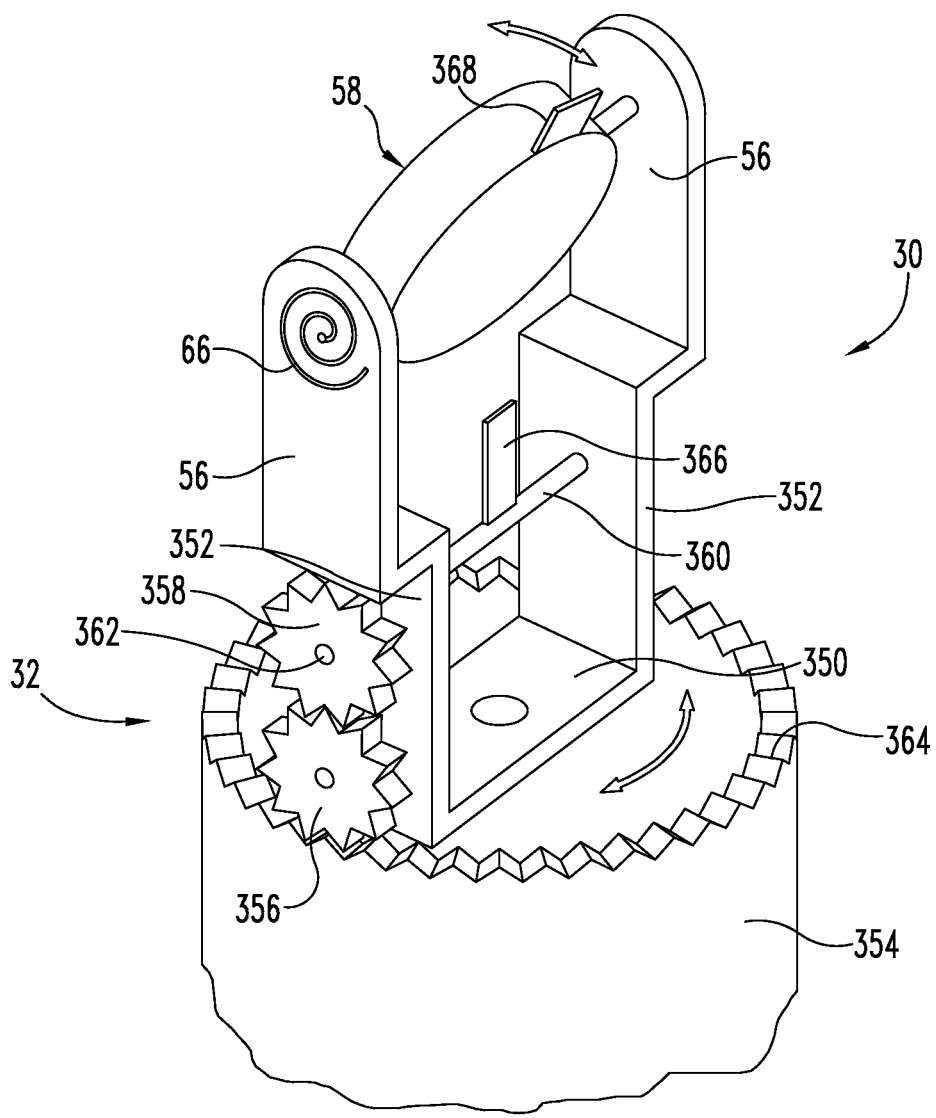
FIG. 9 is an illustrative partial perspective view of the pivot mechanism of FIG. 1 showing an alternative driving mechanism.

A further alternative embodiment is shown in FIG. 9. In this embodiment, pivot mechanism 30 includes arms 56 and base 350. Pivot element 58 including transducer 28 is pivotally mounted to arms 56 as previously described. Base 350 is mounted to bearing 34 (not shown) so that it is rotatable about the rotation axis. Arms 56 and base 350 form a portion of the gimbal-type mounting (or yoke). Lower portions 352 of arms 56 connect the application side end of arms 56 to base 350. Lower portions 352 are disposed generally radially inward from the application side ends of arms 56. In this embodiment, driving mechanism 32 includes face gear 354, pinion 356 (or external gear), and spur gear 358 (or external gear). An axle 360 extends between lower portions 352 and is rotationally mounted to lower portions 352 according to a variety of known methods. End 362 of axle 360 extends through a hole in one of the lower portions 352. Spur gear 358 is operatively connected to axle 360 via end 362 so that spur gear 358 rotates in response to rotation of axle 360. In that way, spur gear 358 is rotationally mounted relative to lower portions 352. Pinion 356 is rotationally mounted to one of lower portions 352 adjacent to spur gear 358. Pinion 356 and spur gear 358 are each toothed and are positioned so that their respective toothed portions are interengaged. Face gear 354 has a toothed face 364 which faces generally in the axial direction relative to the rotation axis. Toothed face 364 is sized and positioned to engage with the toothed face of pinion 356. Face gear 354 is mounted to the inside surface of wall 24 of catheter 22 so that it is fixed relative to catheter 22. Alternatively, face gear 354 can be integrated into or with wall 24.

A tab 366 is mounted to a central portion of axle 360. In this embodiment, pivot element 58 includes a second tab 368. Tab 368 is positioned at a circumferential edge of pivot element 58. In the illustrated embodiment, tab 368 is mounted nearest to the magnetic layer 68 of pivot element 58. In other embodiments, tab 368 could be mounted closer to the transducer 28 side of pivot element 58. Tab 366 is positioned within the pivot path of tab 368 so that tab 368 strikes tab 366 when pivot member 58 pivots towards an end of its pivot range. In other embodiments, tab 366 is positioned within the path of pivot member 58 so that pivot member 58 strikes tab 366 when the pivoting.

During operation (more specifically during a driving pivot stroke) when pivot member 58 causes tab 368 to strike tab 366, tab 366 is caused to rotate about the axis of axle 360 and correspondingly axle 360 rotates which causes spur gear 358 to rotate an incremental distance. Rotation of spur gear 358 causes pinion 356 to rotate a corresponding incremental distance in the opposite rotational direction. Rotation of pinion 356 and its engagement with toothed face 364 of face gear 354 causes pinion 356 to move circumferentially about the rotation axis along a path defined by face gear 354. The movement of pinion 356 applies a torque to pivot mechanism 32 which causes pivot mechanism 32 to rotate an incremental distance about the rotation axis.

A spring can be integrated with axle 360 and/or spur gear 358 which biases axle 360 and tends to cause tab 366 to return to the upright or neutral position (FIG. 9). Tab 368 is configured to cause tab 366 to move a sufficient amount for adequate rotation of pivot mechanism 32 about the rotation axis while also allowing tab 366 to return to the neutral position after pivot member 58 reaches the end of its pivoting range and changes its pivoting direction. Driving mechanism 32 can include a ratcheting component which prevents spur gear 358 from advancing further than a desired incremental distance for each engagement between tab 366 and tab 368. In some embodiments, the ratcheting component includes a small pin with a spring. When tab 368 impacts tab 366, the pin is sprung so that it pushes in between gear teeth and prevents excessive rotation, yet sufficient torque on the gear from a further impact between tab 368 and tab 366 pushes the pin back out against the spring. The relative sizes of spur gear 358 and pinion 356 can be varied in order to achieve a desired incremental rotational distance for each impact between tab 368 and tab 366. In that way, specific incremental rotation of pivot mechanism 32 can be achieved.

Controls for the energizing of coil 80 may be provided to maintain rotational and pivotal motion of transducer 28 about the rotation and pivot axes at a particular rotational speed or pattern. Similarly, the various embodiments of driving mechanism 32 can be configured to provide particular angular movements about the rotation axis with each driving pivot stroke. Examples of configurations can include but are not limited to varying the flexibility of materials for the stop bars, varying the lengths and sizes of the driving rods, configuring the friction rings with a variety of friction coefficients, varying the size and shape of gear teeth, and varying the size and shape of gears. In this way, various rotational and pivotal speed patterns can be achieved. For example, a relatively slow spin around the rotation axis (e.g. about 1-2 Hz) combined with pivoting around the pivot axis more rapidly, e.g. near a resonant frequency of device 20 can provide good results.

Device 20 facilitates capture of an image through a viewing window which is free from unnecessary acoustic attenuation such as artifacts, obstructions, or errors within the image. For example, positioning of transducer 28 at a location which is on an application side of device 20 ensures that wires or other echogenic materials are not positioned within or across the viewing window of transducer 28, even as transducer 28 rotates a complete 360° rotation about the rotation axis as well as pivoting about the pivot axis. In this way, there are no wires or other reflecting materials which could cause artifacts within the image or block portions of the redirected ultrasound waves. This provides the physician a clear view of the entirety of the viewing window. As used herein, the term "window" includes a substantially obstruction-free pathway throughout the structure of device 20 between transducer 28 and organic fluids or tissue which may be positioned external to device 20 during use.

Device 20 is configured to be used with existing medical devices which are designed for percutaneous, intraluminal, or interstitial procedures. For example, device 20 can be used as or with a variety of catheters for different purposes, e.g. positioned on or within an application side of a catheter, depending on the particular configuration. Parts of device 20 as previously described can be positioned within an existing lumen within the catheter. In an alternative embodiment, device 20 could include an external casing (or sheath) which is similar to catheter 22 having walls 24 but being shortened so as to compactly contain device 20. Device 20 could be mounted externally to a catheter using a variety of mounting devices, glues or other types of arrangements. It will be understood by those skilled in the art that the particular type of mounting procedure for the device 20 to an existing medical device can include a variety of different types of mounting methods. Accordingly, the particular methods described herein are not indicative of any limiting aspects of the usage capabilities of the device 20.

While some of the above discussion concerned specific use in the context of ultrasound system applications, it will be understood that embodiments of device 20 could also be used for a variety of other medical procedures and with a variety of other medical devices. The versatility of the embodiments described herein allows device 20 to be used to guide percutaneous therapeutic interventions such as, for example, embolism coils, stents, filters, graphs, balloons, biopsies, and ministering therapeutics, etc. Device 20 can be used to locate various anatomical landmarks that will be used to correctly place or guided therapy. Typical landmarks include confluences, bifurcations, side branches, nearby vessels, nearby nerves, the heart, and other tissues adjacent to vessels or other orifices containing the transducer. Device 20 can also be used to locate diseased tissue that will be treated or avoided. Device 20 can be used during a biopsy to provide an image of a needle being deployed into tissue. During a TIPS (transjugular intrahepatic portocaval shunt) procedure an image can be produced to allow a physician to watch a needle being placed into the portal vein. For AAA (aortic abdominal aneurysm) graft delivery, device 20 can allow a physician to place a guidewire into a contralateral leg. Device 20 could also be used to image the location of a deployed implantable device both during and after deployment.

Although particular materials were highlighted herein for some components of the device 20, those materials are not intended to be limiting of the types of materials which are suitable to be used in the device 20. Additionally, where materials were not highlighted, a variety of materials could be used such as certain types of metals, polymers, ceramics or other types of materials which are suitable for use in devices for small body cavity applications.

The device 20 could also be used for a variety of other medical procedures and with a variety of other medical devices. It will be understood by those skilled in the art that the particular type of mounting procedure can include a variety of different types of mounting methods. Accordingly, the particular methods described herein are not indicative of any limiting aspects of the usage capabilities of the device 20.

In the use of the terms "rotation" or "rotational," e.g. with respect to a rotational axis, it should be understood that even though rotation often implies an angle change much greater than 360°, the devices disclosed herein may be configured in certain embodiments so that the rotational angle may rotate through angles less than 360°. In some instances the term "pivot" may be considered by some more natural than "rotate" or vice versa, but for the purposes of this application the terms "rotate" and "pivot" are used for clarity to indicate the axis about which a change in angle occurs, not the nature or magnitude of the angle change.

While the disclosure has been illustrated and described in detail in the drawings and foregoing description, the same is to be considered as illustrative and not restrictive in character, it being understood that only the preferred embodiments have been shown and described and that all changes, equivalents, and modifications that come within the spirit of the subject matter defined by following claims are desired to be protected. It will be understood that features or aspects described or indicated with a particular embodiment or structure may also be used with other features, aspects, structures or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical device for insertion into a body of a patient, comprising:
   a transducer for transmitting or receiving or transmitting and receiving ultrasound signals;
   a pivot mechanism rotatable about a rotation axis;
   a pivot member mounted to the pivot mechanism and pivotable along a pivot path that extends about a pivot axis that is substantially perpendicular to the rotation axis;
   a driving mechanism positioned within the pivot path of the pivot member, wherein during rotation about the pivot axis, a portion of the pivot member strikes the driving mechanism and causes the pivot mechanism to rotate about the rotation axis; and
   a sensor arranged to sense a position or movement of the pivot member about the pivot axis.

2. The medical device of claim 1, wherein the medical device is a catheter.

3. The medical device of claim 1, wherein the sensor is arranged to sense a position or movement of a magnetic layer of the pivot member.

4. The medical device of claim 3, wherein the sensor includesا Hall Effect sensor.

5. The medical device of claim 1, wherein the sensor includes an electrical switch.

6. The medical device of claim 1, wherein the sensor includes an encoder.

7. The medical device of claim 1, wherein the sensor includes a potentiometer.

8. The medical device of claim 1, wherein the sensor includes an accelerometer.

9. A system, comprising the medical device of claim 1 and a data processing system in communication with the sensor; and
   wherein the data processing system receives sensor data from the sensor and determines speed or position of the pivot member about the pivot axis from the sensor data.

10. The system of claim 9, comprising a graphical display in communication with the data processing system.

11. The system of claim 9, wherein the data processing system is arranged to control the speed at which the pivot member pivots about the pivot axis using the sensor data.

12. A medical device for insertion into a body of a patient, comprising:
    a transducer for transmitting or receiving or transmitting and receiving ultrasound signals;
    a pivot mechanism rotatable about a rotation axis;
    a pivot member mounted to the pivot mechanism and pivotable along a pivot path that extends about a pivot axis that is substantially perpendicular to the rotation axis;
    a driving mechanism positioned within the pivot path of the pivot member, wherein during rotation about the pivot axis, a portion of the pivot member strikes the driving mechanism and causes the pivot mechanism to rotate about the rotation axis; and
    a sensor arranged to sense a position or movement of the pivot mechanism about the rotation axis.

13. The medical device of claim 12, wherein the medical device is a catheter.

14. A system, comprising the medical device of claim 12 and a data processing system in communication with the sensor; and
    wherein the data processing system receives sensor data from the sensor and determines speed or position of the pivot mechanism about the rotation axis from the sensor data.

15. The system of claim 14, comprising a graphical display in communication with the data processing system.

16. A catheter, comprising:
    a transducer for transmitting or receiving or transmitting and receiving ultrasound signals;
    a pivot mechanism rotatable about a rotation axis;
    a pivot member mounted to the pivot mechanism and pivotable along a pivot path that extends about a pivot axis that is substantially perpendicular to the rotation axis;
    a sensor arranged to sense a position or movement of the pivot member about the pivot axis;
    an engagement surface positioned cylindrically and concentric to the rotation axis; and
    a driving mechanism positioned to engage the pivot member and the engagement surface; and
    wherein the pivot member is pivotable through a range bounded by the driving mechanism, wherein during pivotal rotation of the pivot member, abutment of the pivot member against the driving mechanism moves the driving mechanism to engage the engagement surface to create a reactionary force which causes the pivot mechanism to rotate about the rotation axis.

17. A system, comprising the catheter of claim 16 and a data processing system in communication with the sensor; and wherein the data processing system receives sensor data from the sensor and determines speed or position of the pivot member about the pivot axis from the sensor data.

18. The system of claim 17, comprising a graphical display in communication with the data processing system.

19. The system of claim 17, wherein the data processing system is arranged to control the speed at which the pivot member pivots about the pivot axis using the sensor data.

20. The catheter of claim 16, wherein pivoting of the pivot member about the pivot axis rotates the pivot mechanism and the pivot member about the rotation axis relative to a catheter wall of the catheter.

\* \* \* \* \*